United States Patent [19]

Salpeter

[11] Patent Number: 5,550,053

[45] Date of Patent: Aug. 27, 1996

[54] METHOD OF CALIBRATING AN AUTOMATIC CHEMICAL ANALYZER

[75] Inventor: Jerome Salpeter, Yorktown, N.Y.

[73] Assignee: SI Industrial Instruments, Inc., Hawthorne, N.Y.

[21] Appl. No.: 368,853

[22] Filed: Jan. 5, 1995

[51] Int. Cl.[6] .................................................. G01N 31/00
[52] U.S. Cl. ................................. 436/8; 436/52; 436/53; 436/164; 422/67; 422/81; 422/82; 73/1 R; 250/252.1; 356/408; 356/410; 356/436
[58] Field of Search ................................ 436/8, 52, 53, 436/164; 422/81, 82, 62, 67, 68.1, 82.05, 82.09; 73/1 R; 250/252.1; 356/408, 409, 410, 436

[56] References Cited

U.S. PATENT DOCUMENTS

| | | | |
|---|---|---|---|
| 3,634,868 | 1/1972 | Pelavin et al. | 364/571.05 |
| 3,960,497 | 6/1976 | Acord | 422/67 |
| 3,970,392 | 7/1976 | Figueroa et al. | 356/408 |
| 3,992,109 | 11/1976 | Bock | 356/410 |
| 4,043,756 | 8/1977 | Sommervold | 436/43 |
| 4,158,545 | 6/1979 | Yamashita et al. | 436/47 |
| 4,313,735 | 2/1982 | Yamashita et al. | 436/47 |
| 4,536,369 | 8/1985 | Sakurada et al. | 422/65 |
| 4,539,296 | 9/1985 | Manabe | 436/47 |
| 4,545,957 | 10/1985 | Vanhumbeeck et al. | 422/81 |
| 4,558,953 | 12/1985 | Yamada et al. | 356/409 |
| 4,678,755 | 7/1987 | Shinohara et al. | 436/43 |
| 5,183,761 | 2/1993 | Freeman et al. | 436/8 |
| 5,204,264 | 4/1993 | Kaminer | 436/8 |
| 5,230,863 | 7/1993 | Salpeter | 42/67 |
| 5,258,308 | 11/1993 | Freeman et al. | 436/8 |
| 5,348,889 | 9/1994 | Terashima et al. | 436/8 |
| 5,424,212 | 6/1995 | Pinsl-Ober et al. | 436/43 X |

*Primary Examiner*—Jill Warden
*Assistant Examiner*—Maureen M. Wallenhorst
*Attorney, Agent, or Firm*—Darby & Darby, P.C.

[57] ABSTRACT

A method for calibrating an automatic chemical analyzer whereby an improved baseline value is calculated. The analyzer uses a photodetector to detect the amount of light passing through a flow cell and correlates this value to the amount of analyte present in a sample solution. In the preferred embodiment, silica is the analyte under investigation. A baseline solution of a specified (preferably zero) analyte concentration, or a sample solution of unknown analyte concentration, is introduced into a chemical module after chemical reagents have reacted with themselves to form a color complex. The resulting solution is passed to the photodetector which determines the amount of analyte present. This value corresponds to the analyte contaminants within the reagents and can be subtracted out by further calculations.

15 Claims, 3 Drawing Sheets

METHOD OF CALIBRATING AN AUTOMATIC CHEMICAL ANALYZER

This invention relates to a method for calibrating a colorimetric analyzer capable of continuously measuring the concentration of the preselected analyte in a flow of liquid. In particular, this invention relates to an improved method for obtaining a baseline calibration value that is not detrimentally affected by the presence of contaminants in reagents used in the color forming reaction.

BACKGROUND OF THE INVENTION

In power plants, it is necessary to monitor the concentration of soluble silica compounds in the water fed to and in the boilers. Excessive amounts of such compounds (referred to hereinafter as "silica") can cause coating of the turbine blades which requires costly maintenance on a periodic basis. Typically, silica concentrations in excess of 20 parts per billion (ppb) are considered excessive.

Analyzers have been sold for continuously monitoring the concentration of silica and other chemical compositions in water and other fluids. One such device was manufactured and sold by Orion Scientific Instruments of Hawthorne, N.Y. as the Orion Model 1830 Silica Analyzer (hereinafter referred to as the Orion analyzer).

The Orion analyzer coupled a sample of water to be analyzed to a chemical cartridge where known reagents were added and mixed in proper sequence to yield a heteropoly blue complex, the intensity of which was proportional to the silica concentration. The heteropoly blue complex was then pumped to a flow cell positioned in a colorimeter of the type shown in U.S. Pat. No. 4,273,449 of Schmid entitled "Radiation Measuring Apparatus."

This colorimeter directed light through the flow cell and through a reference path so that adjustments for changes in the optical signals could be accommodated. In accordance with known procedures, a baseline value (corresponding to a zero silica content) and a full scale value could be entered into storage in a microprocessor which would then calculate a calibration curve.

The present invention is directed to an improvement over the automatic chemical analyzer disclosed in U.S. Pat. No. 5,230,863 which is incorporated by reference herein. As disclosed in the '863 patent, a computer controlled valving arrangement couples either the solution to be tested, a baseline solution, or a standard (full scale) solution to a chemical cartridge through a pumping mechanism which also feeds the desired reagents to the cartridge. In the preferred embodiment of the invention, the chemical under investigation is silica. Therefore, the desired reagents are: 1) sulfuric acid to acidify the solution; 2) ammonium molybdate to react with the acidified solution to yield a silicomolybdate complex; 3) oxalic acid to inhibit any further reaction from taking place and to prevent phosphate interference; and 4) ascorbic acid to reduce the silicomolybdate complex to a heteropoly blue complex. When the reaction is complete, the solution is directed to a flow cell which includes a chamber having walls through which the desired light source is passed to a detector such as a photodiode. The transmittance of the heteropoly blue complex is measured by the detector to determine the silica content of the solution. The baseline solution and standard (full scale) solutions are first passed through the flow cell automatically and the values of the light intensities for each is stored in memory in the computer. The computer calculates the calibration curve from these values so that thereafter, as the sample is tested, the voltages detected can be correlated within the computer to specific chemical concentrations.

The '863 patent establishes the baseline value by measuring the silica content of the baseline plus reagents solution, with and without the color reagent, the assumption being that the color reagent introduces silica contamination into the measured baseline solution. However, by diverting the color reagent away from the chemical module, and thus, away from the measuring chamber of the flow cell, the composition of the solution under investigation is concentrated resulting in a "dilution error." This "dilution error" may result in inaccurate baseline determinations. Further, the automatic chemical analyzer disclosed in the '863 patent did not fully account for silica contamination as a result of the reagents themselves.

SUMMARY OF THE INVENTION

In accordance with the invention, the baseline value is determined by introducing either the baseline or the sample solution into the chemical chamber after the oxalic acid has been introduced, and therefore, after the reaction forming the coloring agent has been inhibited. By so doing, any silica contamination measured by the detector must have been introduced into the solution by the reagents, and before the baseline or sample solution was added. Thus, the baseline value is measured taking into account the silica contamination introduced by the reagents. These trace amounts will be subtracted out during computer calibration.

Further, the present invention avoids the "dilution error" introduced when a reagent is diverted from the chemical module, as is practiced in the '863 patent. This invention ensures that the concentration of the reagents in the flow cell remains constant during the baseline determination, the standard determination, and the sample determination.

THE DRAWINGS

The foregoing and other features of the present invention will be more readily apparent from the following detailed description and drawings of an illustrative embodiment of the invention which:

FIG. 1 a diagrammatic block diagram showing the mechanical and electrical components of a preferred embodiment of the invention;

DETAILED DESCRIPTION

An analyzer, in accordance with the invention, can be used in any continuous process wherein reagents are mixed with a continuous stream of a liquid to be tested. For purposes of explanation only, the invention is described as it would be used to test for the presence of soluble silicates (silica) for example in power plants where the presence of such silicates is undesirable because of their tendency to coat the turbine blades.

In a typical industrial use, it may be desirable to maintain the level of silica at less than 20 ppb. In such a case the full scale value typically may be in the order of 100 ppb. The principles of the invention are not restricted to any particular type of chemical analysis nor, of course, to a particular range. For purposes of explanation only, the preferred embodiment described as part of an automated continuous system for measuring the amount of silicate present in a continuous flow of water (e.g., from a power plant).

Figure 1:
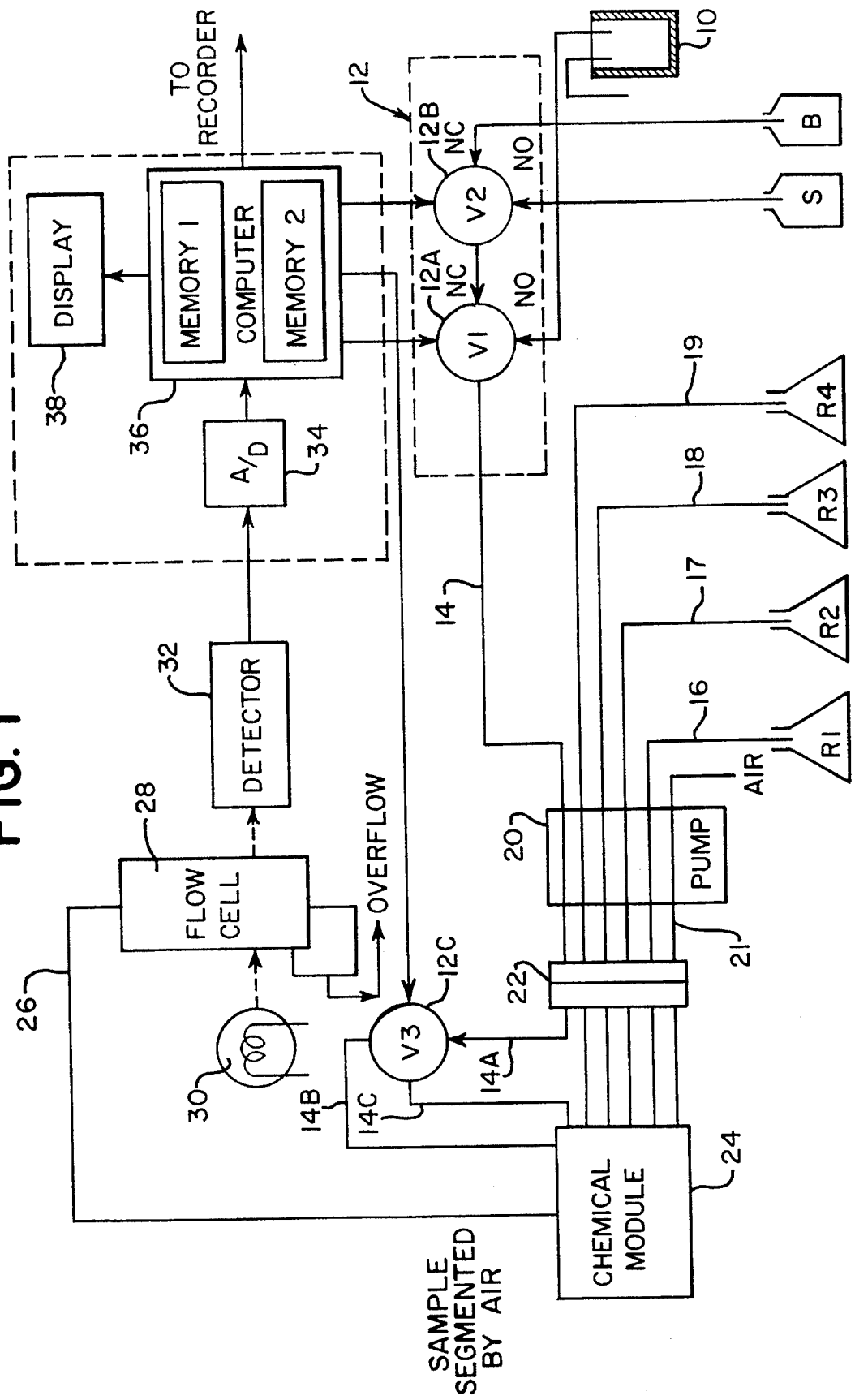

In FIG. 1 the fluid flow is represented by heavy lines and the electrical connections by lighter lines.

The typical reaction for detecting silicates involves four reagents: sulfuric acid, ammonium molybdate, oxalic acid and ascorbic acid. These reagents are held in four containers R1, R2, R3 and R4, respectively. The standard solution is held within a container S and the baseline solution in a container B. The water to be monitored is filtered to remove particulate matter and fed to an overflow sampler 10 which may be of a known construction and provides a continuous stream of water to the analyzer.

The liquid outputs from the overflow sampler 10, the standard container S and the baseline container B are coupled to solenoid controlled valves 12A and 12B which, as explained below, connect one of these three containers to an output tube 14 at appropriate times during the analyzer cycle. Output tube 14 along with the tubes 16–19 from reagent containers R1–R4, respectively are pressed beneath the roller of a peristaltic pump 20 through a disconnect device 22 to a chemical module where the chemical reaction takes place.

Peristaltic pumps are known devices for providing pockets of fluid. Pump 20, for example, may have the construction shown in U.S. Pat. No. 4,233,001 of Schmid entitled "Peristaltic Pump." As shown in the '001 patent, the rotation of a roller occludes the tubes which pass beneath it creating a pressure differential which results in a steady pumping action causing pockets of fluid to pass through the tubes. In the preferred embodiment, tubes 14 and 16–19 are color coded to identify the reagent or solution, and the tubes are held in a predetermined spaced relationship by means of collars or the like (not shown). An air tube 21 open to atmosphere provides the air that is pumped into the line to separate the liquid flow into a multiplicity of segments. The disconnector 22 also is a commercially available device which provides a convenient means for connecting the chemical module 24 to the tubes 14, 16–19 and 21.

Chemical module 24 also may be of known construction. The module comprises an insulated heater housing adapted to receive a removable sealed chemistry cartridge (not shown). The chemical cartridge is sealed to prevent breakage and to provide for better temperature control. The purpose of the cartridge is to direct the chemistry, i.e., to add the various reagents from tubes 16–19 at the proper time, to mix the reagents and the sample or solutions from valve 12A and 12B, and to provide the necessary delays for the reactions to take place. Such devices are known including, in particular, devices for directing the chemistry required to detect the presence of silica in power plants. The output from the cartridge passes through a tube 26 to a flow cell 28 in the form of a segmented stream with each segment separated by small air bubbles pumped through tube 21.

As the reagent and samples are passed through the chemical cartridge within the module 24, a chemical reaction takes place. The sample is first acidified with sulfuric acid and then reacted with ammonium molybdate to yield a silicomolybdate complex. The oxalic acid breaks up the phosphomolybdate complex but does not affect the silicomolybdate complex. This inhibits the reaction from progressing any further. Ascorbic acid then reduces the silicomolybdate complex to a heteropoly blue complex which is blue-green in color. As is well known, the absorbance (transmittance) of the heteropoly blue complex can be measured by passing light at a wavelength at 820 nanometers (nm) or 660 nm through the liquid and detecting the amount of light passing through the sample. The detector output provides an indication of the silica content in the sample. This determination is also made in accordance with the '863 patent.

To determine the baseline value according to the preferred embodiment of the present invention, the following steps are followed. The sulfuric acid reagent R1 is introduced into chemical module 24 through line 16. The ammonium molybdate is introduced into chemical module 24 through line 17. The ammonium molybdate R2 reacts with any silica molecules present in the acid solution to form a silicomolybdate complex. Then oxalic acid R3 is added to chemical module 24 through line 18 to halt the reaction and inhibit the further formation of silicomolybdate complex. After the oxalic acid R3 has been added, baseline solution from container B of known zero (0) ppb silica content is introduced into the chemical module. This is accomplished by: 1) energizing solenoid controlled valves 12A and 12B to allow the baseline solution to enter line 14; and 2) activating a third solenoid controlled valve 12C, connected between disconnector 22 and chemical module 24 in line 14, to divert the baseline solution in line 14 so that the baseline solution passes up through port 14A of the solenoid controlled valve 12C, out through port 14B, and into chemical module 24. Ascorbic acid R4 is then added. The ascorbic acid R4 reacts with the solution to reduce the silicomolybdate complex (if present) to the heteropoly blue complex. The solution is finally sent through flow cell 28 where the transmissivity of the heteropoly blue complex is measured to determine the silica content. (This process is explained in detail below.) The baseline value is stored in computer 36. Because the baseline solution is introduced into chemical module 24 after the color reaction has been inhibited by oxalic acid R3, any silica present in the baseline mixture and detected by flow cell 28 is attributable to silica contamination from reagents R1 and R2. These trace amounts of silica within the sulfuric acid R1 and the molybdate reagent R2 are recorded as part of the baseline value during the computers' calculations for baseline calibration. Color contamination from the reagents will be subtracted out during further computer calibration calculations.

Unlike the '863 patent, the color reagent is not diverted away from chemical module 24 during the determination of the baseline value. Consequently, the concentrations of the reagents remain constant as the baseline mixture passes from chemical module 24 and into flow cell 28. Therefore, the baseline mixture is not concentrated, and any change in the silica detected is due to an actual change in the silica present, and not due to the change in the concentration of the reagents present in the baseline mixture.

In a preferred embodiment of the invention, the baseline value may also be determined while the sample solution is being passed through the chemical module 24. Because the solenoid controlled valve 12A is already activated, the only additional step required is to activate solenoid controlled valve 12C. This diverts the sample solution up through port 14B and into the chemical module 24 after the oxalic acid R3 has inhibited any further formation of the silicomolybdate complex. Because the sample solution is introduced into the chemical module 24 after the color reaction has been inhibited by the oxalic acid R3, the only silica detected by the flow cell 28 is attributable to silica contamination from reagents R1 and R2.

The standard value is determined as follows. Solenoid controlled valves 12A and 12B are activated to introduce standard solution into line 14. Solenoid controlled valve 12C is not activated allowing the standard solution to flow up through port 14A of the solenoid controlled valve 12C, out through port 14C, and into chemical module 24 before the reagents are added. After the standard solution enters chemical module 24, the sulfuric acid R1 is introduced into chemical module 24. Sulfuric acid reagent R1 acidifies the standard solution. Ammonium molybdate R2 is introduced into chemical module 24 through line 17 and reacts with the silica present in the acid solution to form a silicomolybdate complex. Next, oxalic acid R3 is added to chemical module 24 through line 18 to halt the reaction and inhibit the further formation of silicomolybdate complex. Ascorbic acid R4 is introduced through line 19 to form the heteropoly blue complex. The resulting solution is then sent to flow cell 28 where the transmissivity of the heteropoly blue complex is measured to determine the silica content. (This process is explained in detail below.) This standard value is also stored in computer 36. Computer 36 then calculates the calibration curve as outlined below.

As detailed in the '863 patent, a preferred embodiment of the flow cell 28 is described below with respect to FIGS. 2–4. One function of the flow cell 28 is to debubble the output from the chemical module in tube 26. The flow cell 28 also prevents foam produced by any wetting agents in the solution from affecting any readings. Such wetting agents are used to minimize back pressure due to the relatively narrow bore tubing used in the preferred embodiment and, typically, are added to the reagents. In addition, the flow cell 28 provides a constant level device from the constantly flowing stream of water.

A light source shown at 30 directs light at the desired wavelength (e.g., 820 nm) through the measuring chamber of the flow cell 28 where it is detected by detector 32. Detector 32 produces a voltage output which is proportional to the amount of light passing through the flow cell (and, therefore, the quantity of silica in solution).

The analog voltage from detector 32 is connected to an analog to digital converter 34 which couples its digital output to a computer 36, e.g., a microprocessor. Computer 36 is programmed, as explained below, to provide an output indicative of the quantity of silicate in the sample. This output may be displayed on a display device 38 and it may also be transmitted to a recorder to maintain a permanent record. In addition, the computer 36 provides timing signals to the solenoid operated valves 12A, 12B and 12C to determine which of the standard, baseline or sample solutions is to be fed into tube 14, and to determine whether valve 12C is to divert the baseline solution or the sample solution in order to introduce the baseline solution or the sample solution into chemical module 24 after oxalic acid R3 has been introduced into chemical module 24.

As described in the '863 patent the sample is analyzed via a completely automatic system. To do this, a reference is set up within the computer 36 so that the measured values of light absorbance can be compared to the reference values to determine the silica content. The baseline solution in container B is a solution made as free of silica as possible (e.g., 0 ppb). The standard solution in container S is the full scale value of the analyzer and it will be set by the operator. For example, if it is desired to maintain a silica content of less than 20 ppb, a standard solution may be prepared in which the silica concentration is 100 ppb. As now explained, during the initializing process, the computer 36 stores in memory the values of the output signals from detector 32 corresponding to both the baseline and standard solutions. Since the relationship of light absorbance in flow cell 28 to silica concentration is linear, the output of the detector 32 can be compared with the values stored in the computer 36 for the baseline and standard solutions and the silica concentration calculated and displayed.

The operation of the system is as follows. First, the system determines the baseline value and stores this value in the computer 36. Next, the standard value is determined and similarly stored. The calibration curve is then calculated so that the value determined from the sample solution may be compared against the calibration curve to determine the silica content in the sample solution. In detail, the reagent bottles R1–R4 and the standard and baseline containers S and B are filled with the proper solutions. The overflow sample 10 is coupled to a port in the plant so that the sample to be measured is available at the input to the valve 12A. The user then pushes a button to start the operation. Immediately, computer 36 causes valves 12A and 12B to connect the baseline solution within container B to tube 14. Valve 12C is also activated to divert the baseline solution so that the baseline solution passes up through port 14A of the solenoid controlled valve 12C, out through port 14B, and into chemical module 24. The baseline solution is, thereby, introduced into chemical module 24 after the oxalic acid has inhibited the formation of the molybdosilicic acid complex. Simultaneously, pump 20 is turned onto high speed for the purpose of pumping the reagents and baseline solution into the analyzer as quickly as possible. For example, pump 20 may normally operate at 2.8 rpm; at high speed, it may operate at 9 rpm.

After a period of six minutes, the computer causes the pump 20 to operate at normal speed for sixteen minutes. At the end of this initial period (twenty-two minutes in this example) the baseline solution plus reagents fully occupy the flow cell 28 so that the analyzer is measuring the light through the flow cell when the silica concentration is at the calibrated zero. This value is converted to digital form and stored in memory M1 within computer 36.

The computer then actuates the solenoid operated valves 12A and 12B to couple the standard solution in container S to the tube 14. Pump 20 is simultaneously caused to operate at high speed until the standard solution reaches the chemical module 24, for example, three minutes. For any given system, of course, this time interval is known and can be programmed into the computer. This is accomplished by not activating Valve 12C, thereby allowing the standard solution to flow up through port 14A of the solenoid controlled valve 12C, out through port 14C, and into chemical module 24 before the reagents are added. After the standard solution enters chemical module 24, the reagents are added in the proper order and the reaction is allowed to take place.

Once the standard solution is in the chemical module 24, the computer returns pump 20 to normal speed. At normal speed, in the preferred embodiment, it may take about sixteen more minutes to replace the baseline solution in the flow cell 28 with the standard solution flowing from the chemical module 24.

When this time interval has passed, the intensity of the light passed through the flow cell 28 represents the silica content of the known standard. Accordingly, this value is sensed by the detector 32, converted to digital form in converter 34 and stored in memory M2.

Knowing the values for the baseline and standard solutions, the computer establishes a calibration curve in accordance with known procedures. For example, if the output of detector 32 is at a certain value at 0 ppb and a second value at 100 ppb and if there is a linear relationship between detector output and silica content (or if the shape of the curve is otherwise known) then whatever the value of the output of detector 32, the computer 36 can calculate the silica content for display and/or recording or other purposes.

After the calibration curve has been stored in the computer, the computer then signals the solenoid control valve 12A to couple the overflow sampler 10 to the tube 14. In this condition, the analyzer continuously analyzes the flow of sample through the overflow sampler 10 for silica content.

At predetermined intervals, the computer 36 will cause the solenoid controlled valve 12C to be activated. This introduces the sample solution in container 10 into the chemical module 24 after the oxalic acid reagent R3. Because the amount of silica detected is solely due to the reagents, this process allows the computer 36 to quickly update the baseline value and to automatically shift the calibration curve if the baseline value has changed.

Periodically, for example every eight or twelve hours, the computer 36 will cause the solenoid controlled valves 12A, 12B, and 12C to be activated. This will introduce the baseline solution in container B into the chemical module 24 after the oxalic acid reagent. When this occurs, the pump once again operates at high speed for about six minutes followed by sixteen minutes at normal speed so that a new baseline calibration can be determined. If the baseline value has changed, the calibration curve is again "shifted" automatically by the computer such that the concentration of the baseline solution as measured on the calibration curve is returned to the previously measured value. The change in absorbance may be caused by temperature changes, electronic drift in the equipment, and/or degradation of the reagents which may decrease sensitivity of the system.

At still longer periodic intervals, both the baseline and standard or full scale values are calculated and stored in memory. For example, every forty-eight hours the entire process may be recycled.

Figure 2:
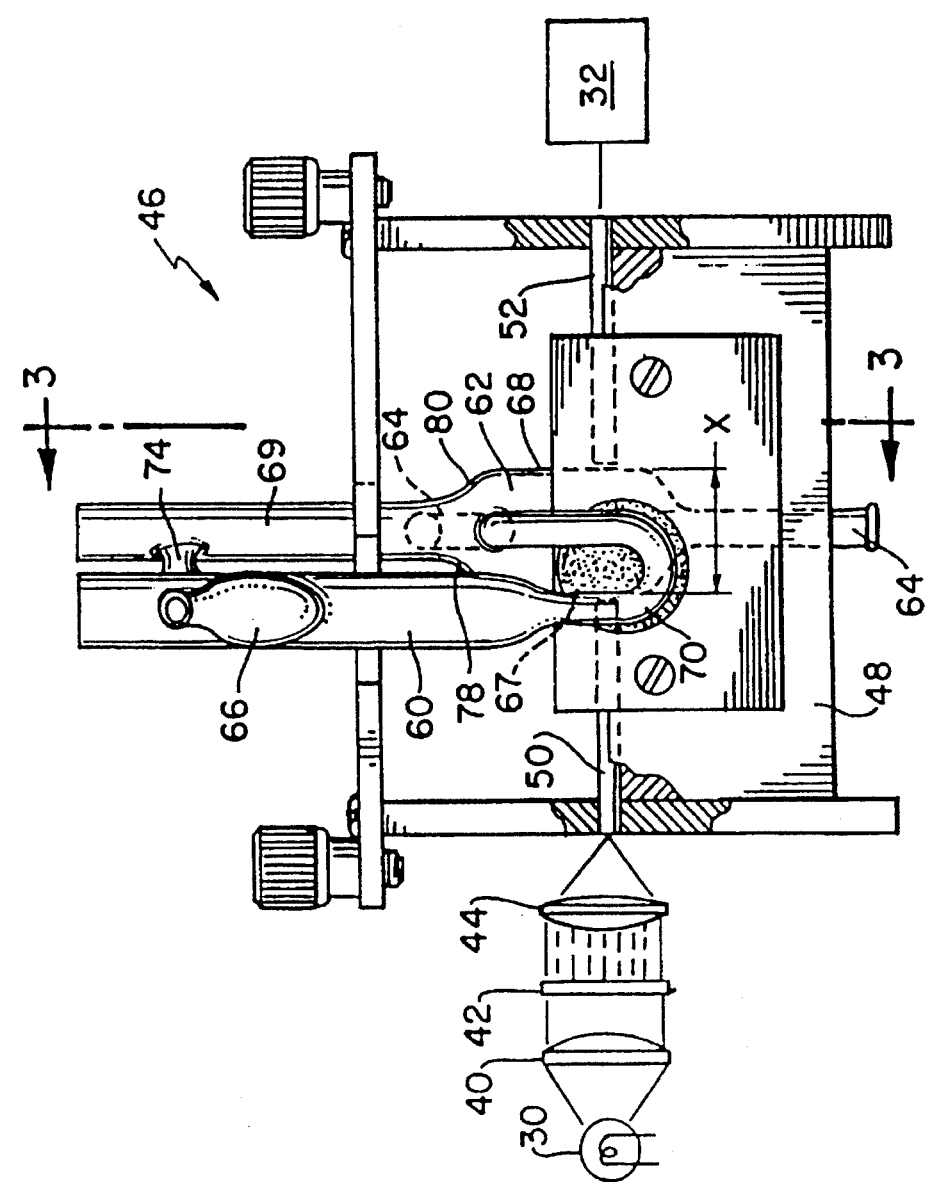
FIG. 2 illustrates diagrammatically the optical train of a colorimeter in accordance with a preferred embodiment of the invention in conjunction with a front plan view of a flow cell and the mechanical structure used to support the flow cell.

The optical train according to a preferred embodiment of the invention is shown in FIG. 2. The light output from source lamp 30 is coupled through a collimating lens 40, an interference filter 42 and a condenser lens 44. The filter 42 removes all but the desired wavelength, 820 nm in this example. Reasonably collimated light is necessary since the interference filter can be made efficiently for only a restricted angle of incidence.

The flow cell 28 is held in a support assembly 46 which includes a firmly supported bracket 48 adapted to securely hold light pipes 50 and 52 in suitable V grooves (not numbered). The light pipes 50 and 52, arranged on opposite sides of the flow cell 28, direct the filtered light from condenser lens 44 through the liquid within the flow cell to detector 32, typically a photodiode.

In a preferred embodiment of the invention, the collimated light is split into two beams. The first beam is directed through the flow cell 28 to detector 32. The second beam is directed through a reference channel (not shown) to a second detector (not shown). This allows any changes in the light source to be monitored and corrected for.

Condenser lens 44 functions as a decollimator and should have a high numerical aperture to minimize energy losses due to diffusion. The condenser lens focuses the available light energy onto the entrance face of the light pipe 50. The light pipes 50 and 52 are able to direct the light with minimal losses to the active portion of the cell and then direct the attenuated light out to the active photodetector surface.

In operation, light enters the front face of the entrance light pipe 50 of the flow cell and is directed onto the entrance surface of the flow cell proper. The colored sample absorbs a fixed portion of the nominally-monochromatic light. The attenuated light is then directed out through the exit light pipe 52.

All the light from the exit face of the flow cell strikes the active surface of the solid-state photodetector 32. The detector converts impinged light from 340 to 900 nm into a corresponding electrical signal which is processed in the electronics package. The optical train and detectors respond accurately in the typically linear Beer-Lambert relationship between absorbance and concentration.

Energy losses in the optical system are minimized by careful design and selection of optical components. Less energy is lost with the use of a single large-diameter, high through-put narrow-band optical filter than a conventional, small-diameter dual filter system.

Figure 3:
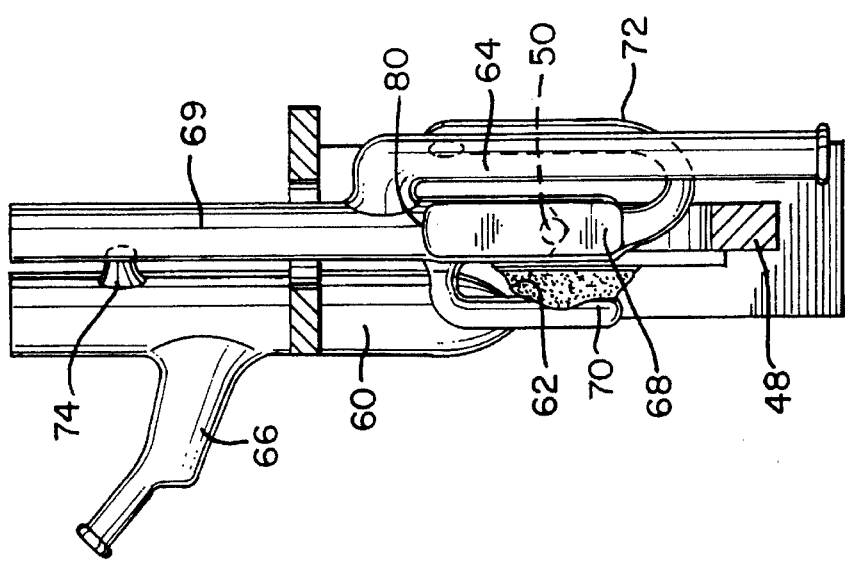
FIG. 3 is a front view of the flow cell.
Figure 4:
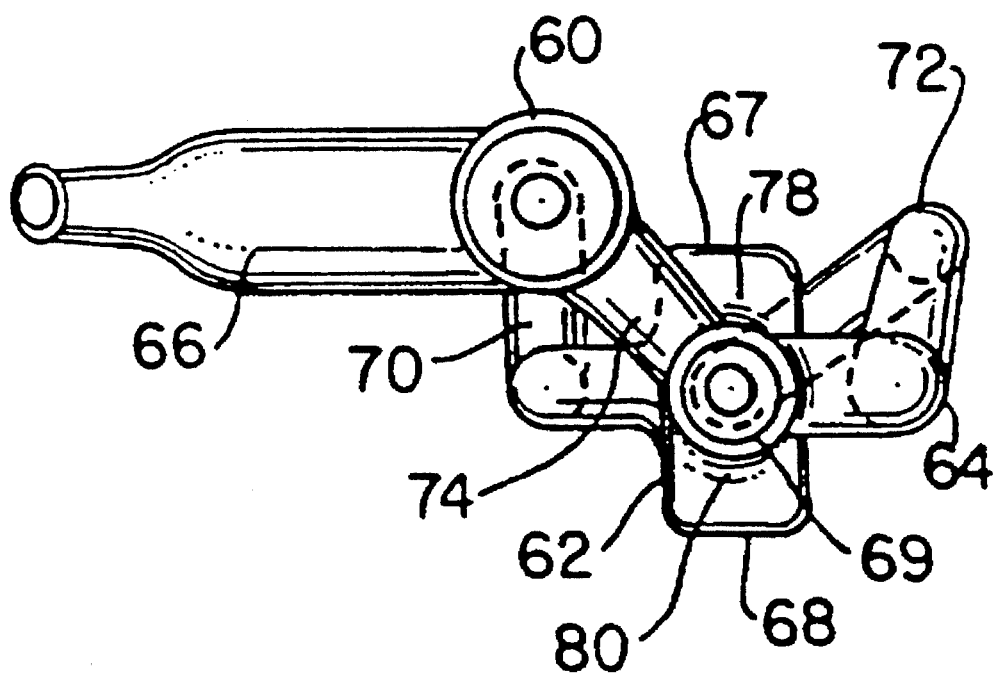
FIG. 4 is a top view of the flow cell.

As shown in FIGS. 2–4, the flow cell which may be made of glass includes a reservoir 60, a measuring chamber 62 and an overflow pipe 64. An inlet pipe 66 introduces the liquid to be tested into the vertical reservoir 60. The measuring chamber 62 is essentially vertical in cross-section and as shown in FIG. 3 includes opposing sides 67 and 68 and a venting tube 69 open to atmosphere. The light from lamp 30 passes through the sides 67 and 68 which are polished to minimize reflections and optical losses. The liquid within reservoir 60 is fed through a U-shaped tube 70 into the upper portion of the measuring chamber 62 of the flow cell (see FIG. 2). The liquid from the measuring chamber 62 is coupled to the overflow pipe 64 by means of a similarly U-shaped tube 72. This particular configuration shown in FIGS. 2–4 is used in the preferred embodiment of the invention because it is adapted to be conveniently retained within the existing support carriage of the Orion analyzer but, as explained in the '863 patent, the only critical structural aspects of the flow cell reside in the shape of the measuring chamber 62 and its relation to the venting tube 69.

As is well-known from the Beer-Lambert formula, light absorbance (transmissivity) is dependent upon the length of the light path through the flow cell or, in this case, the distance between the surfaces 67 and 68 as represented by the dimension X in FIG. 2. For very low chemical concentrations, the dimension X should be as large as possible. However, because of the need to vent the system of air bubbles among other things, there is a practical limit on the length of dimension X.

The air bubbles that create segmented flow to the flow cell 28 permit sample-to-sample discretion thereby enhancing the response time by avoiding averaging. Also, the air bubbles tend to scrub the walls of the glass tubes and generally improve mixing which are desirable features. As mentioned above, the air bubbles are introduced into the liquid stream by means of the tube 21 which is vented to atmosphere.

The flow cell illustrated in FIGS. 2–4 shows the measuring chamber 62 vented directly to the atmosphere by the tube 69. However, the fact that the measuring chamber is vented creates problems since if the diameter of the venting tube 69 is too large, the flow cell will combine the discrete samples (previously separated by air bubbles) which causes averaging and thus tends to reduce response time. On the other hand, if the size of the vent 69 is too small, the surfaces 67 and 68 of measuring chamber 62 extend outside the walls of the venting tube 69 creating shoulders 78 and 80 where air bubbles tend to collect. If the differential in size is small, the shoulders 78 and 80 can be severely sloped as shown in FIG. 2 to minimize this problem but if the dimension X is large, then it is impossible to simultaneously avoid the problem of averaging and the problem of accumulating air bubbles. Through experiments, it has been discovered that the maximum length of the dimension X is approximately 30 millimeters. At this dimension, the maximum size of the venting tube 69 which will avoid averaging of samples also will allow virtually complete venting of all air within the liquid in the flow cell.

Flow cells with a dimension X of less than 30 mm of course can be used and, in fact, are preferred where concentrations substantially higher than 20 ppb are detected.

I claim:

1. A method for calibrating an automatic chemical analyzer comprising the steps of:
   a.) adding at least a color reagent that reacts with an analyte to form a color complex, and an inhibiting reagent to inhibit any further formation of color complex after a specified time has elapsed, to a chemical module; then
   b.) adding a baseline solution of known analyte concentration to the chemical module to form a baseline mixture that maintains the ratio of the reagents constant;
   c.) passing the baseline mixture through a flow cell;
   d.) passing light at a specified frequency through the flow cell so that the concentration of analyte in the baseline mixture may be determined; and
   e.) calculating a baseline value corresponding to the quantity of the analyte detected in the baseline mixture which also corresponds to the amount of analyte contamination contained within the color reagent and the inhibiting reagent.

2. The method for calibrating an automatic chemical analyzer as described in claim 1 wherein the analyte is silica.

3. The method for calibrating an automatic chemical analyzer as described in claim 2 wherein the color reagent is ammonium molybdate.

4. The method for calibrating an automatic chemical analyzer as described in claim 3 wherein the inhibiting reagent is oxalic acid.

5. A method for calibrating a chemical analyzer according to claim 1, further comprising the steps of measuring concentration of analyte present in the baseline mixture on a periodic basis and adjusting the baseline value whenever the currently measured analyte concentration differs from a previously measured analyte concentration.

6. A method for calibrating an automatic chemical analyzer used to measure the quantities of an analyte within a chemical module, comprising the steps of introducing into the chemical module at least a color reagent which reacts with any analyte present within the chemical module, and an inhibiting reagent to inhibit any further reaction between the analyte and the color reagent after a specified time has elapsed, then adding a sample solution containing an unknown quantity of an analyte into the chemical module to form a sample mixture that maintains the ratio of the reagents constant, determining, via optical means, the quantity of the analyte present in the sample mixture, and then calculating a baseline value corresponding to the quantity of the analyte detected in the sample mixture which also corresponds to the amount of analyte contamination contained within the reagents and within the chemical module.

7. The method for calibrating an automatic chemical analyzer as described in claim 6 wherein the analyte is silica.

8. The method for calibrating an automatic chemical analyzer as described in claim 7 wherein the color reagent is ammonium molybdate.

9. The method for calibrating an automatic chemical analyzer as described in claim 8 wherein the inhibiting reagent is oxalic acid.

10. A method for calibrating a chemical analyzer according to claim 6, further comprising the steps of measuring concentration of analyte present in the sample mixture on a periodic basis and adjusting the baseline value whenever the currently measured analyte concentration differs from a previously measured analyte concentration.

11. A method for calculating a baseline value during the calibration of an automatic chemical analyzer to detect a quantity of an analyte present in a sample solution comprising the steps of:
   a. adding a plurality of reagents, including at least a color reagent to react with the analyte to form a color complex, and an inhibiting reagent to inhibit the further formation of color complex after a specified time has elapsed, to a chemical module; then
   b. adding one of a baseline solution of known analyte concentration and a sample solution of unknown analyte concentration into the chemical module to form a baseline mixture that maintains the ratio of the reagents constant;
   c. passing the baseline mixture through a flow cell;
   d. passing light at a specified frequency through the flow cell so that the concentration of analyte in the baseline mixture may be determined; and
   e. calculating a baseline value corresponding to the quantity of the analyte detected in the baseline mixture which also corresponds to the amount of analyte contamination contained within the reagents.

12. The method for calculating a baseline value during the calibration of an automatic chemical analyzer described in claim 11 wherein the analyte is silica.

13. The method for calculating a baseline value during the calibration of an automatic chemical analyzer described in claim 11 wherein the color reagent is ammonium molybdate.

14. The method for calculating a baseline value during the calibration of an automatic chemical analyzer described in claim 13 wherein the inhibiting reagent is oxalic acid.

15. A method for calculating a baseline value during the calibration of an automatic chemical analyzer described in claim 11 further comprising the steps of measuring concentration of analyte present in the baseline mixture on a periodic basis and adjusting the baseline value whenever the currently measured analyte concentration differs from a previously measured analyte concentration.

* * * * *